United States Patent
Veit et al.

(10) Patent No.: US 7,244,597 B2
(45) Date of Patent: Jul. 17, 2007

(54) SECONDARY LIQUEFACTION IN ETHANOL PRODUCTION

(75) Inventors: Christopher Veit, Wake Forest, NC (US); Claus Felby, Vekso (DK)

(73) Assignees: Novozymes A/S, Bagsvaerd (DK); Novozymes North America, Inc., Franklinton, NC (US)

( * ) Notice: Subject to any disclaimer, the term of this patent is extended or adjusted under 35 U.S.C. 154(b) by 504 days.

(21) Appl. No.: 10/416,393

(22) PCT Filed: Nov. 9, 2001

(86) PCT No.: PCT/DK01/00737

§ 371 (c)(1),
(2), (4) Date: May 9, 2003

(87) PCT Pub. No.: WO02/38787

PCT Pub. Date: May 16, 2002

(65) Prior Publication Data

US 2004/0091983 A1 May 13, 2004

Related U.S. Application Data

(60) Provisional application No. 60/256,015, filed on Dec. 15, 2000, provisional application No. 60/252,213, filed on Nov. 21, 2000.

(30) Foreign Application Priority Data

Nov. 10, 2000 (DK) ............................... 2000 01676
Dec. 11, 2000 (DK) ............................... 2000 01854

(51) Int. Cl.
*C12P 7/06* (2006.01)
*C12P 7/08* (2006.01)
*C12P 7/12* (2006.01)

(52) U.S. Cl. .................. 435/161; 435/99; 435/163; 435/165

(58) Field of Classification Search ................ 435/161, 435/163, 155, 165, 99
See application file for complete search history.

(56) References Cited

U.S. PATENT DOCUMENTS 5,231,017 A 7/1993 Lantero et al.
6,284,498 B1 * 9/2001 Fouache et al. .............. 435/95

FOREIGN PATENT DOCUMENTS

| CA | 1 143 677 | 8/1983 |
| EP | 0 138 428 | 4/1985 |
| WO | WO 96/13600 | 5/1996 |
| WO | WO 99/19467 | 4/1999 |

OTHER PUBLICATIONS

Shetty et al ("Factors Affecting the Economics of Glucose Production," Delivering Innovation Through Biotechnology, Genencor International, Inc., (1998).*
Takasaki et al., Journal of Fermentation and Bioengineering, vol. 77, No. J, pp. 94-96, (1994).
Park et al., Biochimica et Biophisica Actn 1478, pp. 165-185, (2000).
Boel et al., Biochemistry, vol. 29, pp. 6244-6249, (1990).

* cited by examiner

*Primary Examiner*—Herbert J. Lilling
(74) *Attorney, Agent, or Firm*—Elias J. Lambiris

(57) ABSTRACT

The invention relates to a method of producing ethanol by fermentation, said method comprising a secondary liquefaction step in the presence of a thermostable acid alpha-amylase or, a thermostable maltogenic acid alpha-amylase.

19 Claims, 1 Drawing Sheet

SEQUENCE LISTING

```
<160> NUMBER OF SEQ ID NOS: 1

<210> SEQ ID NO 1
<211> LENGTH: 484
<212> TYPE: PRT
<213> ORGANISM: Aspergillus niger
<220> FEATURE:
<221> NAME/KEY: misc_feature
<223> OTHER INFORMATION: SEQ ID NO:1

<400> SEQUENCE: 1

Leu Ser Ala Ala Ser Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asn Glu Ile Tyr Cys Gly Gly Ser Trp Gln Gly Ile Ile Asp His
        35                  40                  45

Leu Asp Tyr Ile Glu Gly Met Gly Phe Thr Ala Ile Trp Ile Ser Pro
    50                  55                  60

Ile Thr Glu Gln Leu Pro Gln Asp Thr Asp Gly Glu Ala Tyr His
65                  70                  75                  80

Gly Tyr Trp Gln Gln Lys Ile Tyr Asp Val Asn Ser Asn Phe Gly Thr
                85                  90                  95

Ala Asp Asn Leu Lys Ser Leu Ser Asp Ala Leu His Ala Arg Gly Met
            100                 105                 110

Tyr Leu Met Val Asp Val Val Pro Asp His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Glu Asp Cys Trp Glu Gly Asp Thr Ile Val Ser Leu Pro Asp Leu
                165                 170                 175

Asp Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Leu Glu Val Gln Pro Asp Phe Phe Pro Gly Tyr Asn Lys Ala Ser Gly
    210                 215                 220

Val Tyr Cys Val Gly Glu Ile Asp Asn Gly Asn Pro Ala Ser Asp Cys
225                 230                 235                 240

Pro Tyr Gln Lys Val Leu Asp Gly Val Leu Asn Tyr Pro Ile Tyr Trp
                245                 250                 255

Gln Leu Leu Tyr Ala Phe Glu Ser Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Lys Tyr
```

-continued

```
            290                     295                     300
Thr Ser Asp Tyr Ser Gln Ala Lys Asn Val Leu Ser Tyr Ile Phe Leu
305                     310                     315                     320

Ser Asp Gly Ile Pro Ile Val Tyr Ala Gly Glu Glu Gln His Tyr Ala
                    325                     330                     335

Gly Gly Lys Val Pro Tyr Asn Arg Glu Ala Thr Trp Leu Ser Gly Tyr
                340                     345                     350

Asp Thr Ser Ala Glu Leu Tyr Thr Trp Ile Ala Thr Thr Asn Ala Ile
            355                     360                     365

Arg Lys Leu Ala Ile Ala Ala Asp Ser Ala Tyr Ile Thr Tyr Ala Asn
        370                     375                     380

Asp Ala Phe Tyr Thr Asp Ser Asn Thr Ile Ala Met Ala Lys Gly Thr
385                     390                     395                     400

Ser Gly Ser Gln Val Ile Thr Val Leu Ser Asn Lys Gly Ser Ser Gly
                    405                     410                     415

Ser Ser Tyr Thr Leu Thr Leu Ser Gly Ser Gly Tyr Thr Ser Gly Thr
                420                     425                     430

Lys Leu Ile Glu Ala Tyr Thr Cys Thr Ser Val Thr Val Asp Ser Ser
            435                     440                     445

Gly Asp Ile Pro Val Pro Met Ala Ser Gly Leu Pro Arg Val Leu Leu
        450                     455                     460

Pro Ala Ser Val Val Asp Ser Ser Ser Leu Cys Gly Gly Ser Gly Arg
465                     470                     475                     480

Leu Tyr Val Glu
```

SECONDARY LIQUEFACTION IN ETHANOL PRODUCTION

CROSS-REFERENCE TO RELATED APPLICATIONS

This application is a 35 U.S.C. 371 national application of PCT/DK01/00737 filed Nov. 9, 2001 (the international application was published under PCT Article 21(2) in English), which claims priority or the benefit under 35 U.S.C. 119 of Danish application nos. PA 2000 01676 filed Nov. 10, 2000, and PA 2000 01854 filed Dec. 11, 2000 and U.S. provisional application Nos. 60/252,213 filed Nov. 21, 2000, and 60/256,015 filed Dec. 15, 2000, the contents of which are fully incorporated herein by reference.

FIELD OF THE INVENTION

The invention relates to a process for producing ethanol.

BACKGROUND OF THE INVENTION

Ethanol has widespread application as an industrial chemical, gasoline additive or straight liquid fuel. As a fuel or fuel additive, ethanol dramatically reduces air emissions while improving engine performance. As a renewable fuel, ethanol reduces national dependence on finite and largely foreign fossil fuel sources while decreasing the net accumulation of carbon dioxide in the atmosphere. Fermentation processes are used for the production of ethanol. There are a large number of disclosures concerning production of alcohol by fermentation, among which are, e.g., U.S. Pat. No. 5,231,017 and CA 1,143,677. EP 138428 mentions an *Aspergillus niger* alpha-amylase preparation for use in liquefaction in the alcohol industry.

There is a need for further improvement of ethanol manufacturing processes.

SUMMARY OF THE INVENTION

The invention relates to a method of producing ethanol by fermentation, said method comprising a secondary liquefaction step in the presence of a thermostable acid alpha-amylase or, a thermostable maltogenic acid alpha-amylase. In particular, is provided an improved method for production of ethanol based on whole grain as the starch containing starting material.

Thus, the invention relates to a method of producing ethanol from a starch containing material, preferably based on whole grain, said method comprising the steps of: (a) liquefaction of a starch containing material in the presence of an alpha-amylase; (b) jet cooking; (c) liquefaction in the presence of a thermostable acid alpha-amylase or, a thermostable maltogenic acid alpha-amylase; and (d) saccharification and fermentation to produce ethanol; wherein the steps (a), (b), (c) and (d) is performed in the order (a), (b), (c), (d).

The process of the invention may also comprise one or more additional steps, before, in between and/or after step (a), (b), (c) and (d), such as, e.g. recovering of the ethanol after step (d).

The invention also relates to products obtained or obtainable by the processes of the invention and to the use of such products, e.g. as fuel alcohol or an additive.

The invention in further aspects relates to use of a thermostable acid alpha-amylase or, a thermostable maltogenic acid alpha-amylase in a secondary liquefaction step in a process for production of ethanol, particularly from whole grain.

DETAILED DESCRIPTION OF THE INVENTION

Ethanol Production

Figure 1:
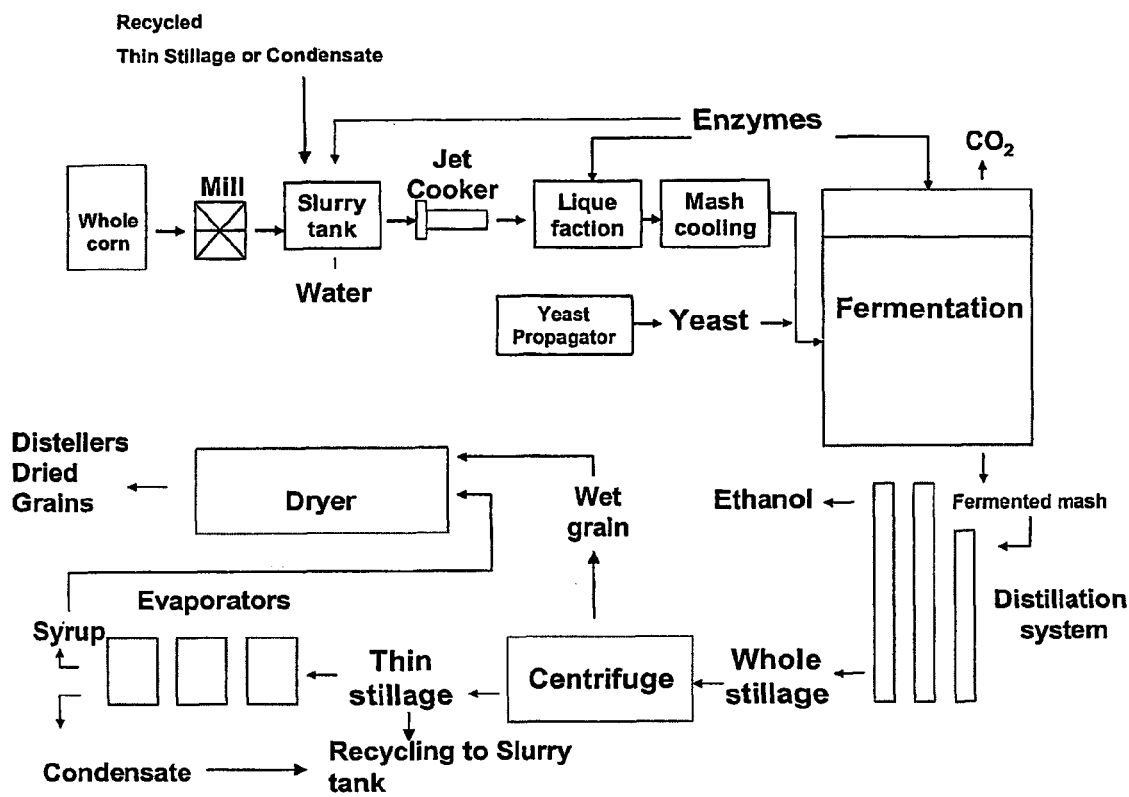
FIG. 1 illustrates a process flow diagram for the preparation of ethanol in accordance with one embodiment of the invention. The primary liquefaction step may be performed by the presence of the enzyme alpha-amylase in the slurry tank while the secondary liquefaction step is termed "liquefaction" on the diagram.

The, present invention provides a process of producing ethanol, in particular improvement of the secondary liquefaction step in a process of producing ethanol from dry milled whole grain.

The invention provides a method of producing ethanol by fermentation, said method comprising a secondary liquefaction step in the presence of a thermostable acid alpha-amylase or, a thermostable maltogenic acid alpha-amylase. A particularly interesting embodiment relates to a fermentation process of the invention where the starting material is whole grain which have been partitioned into finer parts, preferably by dry milling.

Thus, the invention in one aspect relates to a method of producing ethanol from a starch containing material, said method comprising the steps of:

a) liquefaction of a starch containing material in the presence of an alpha-amylase;
b) jet cooking;
c) liquefaction in the presence of a thermostable acid alpha-amylase;
d) saccharification and fermentation to produce ethanol;

wherein the steps (a), (b), (c) and (d) is performed in the order (a), (b), (c), (d).

Raw Material

In one embodiment, the starch containing material is selected from the group consisting of: tubers, roots and whole grain; and any combinations of the forgoing. In one embodiment, the starch containing material is obtained from cereals. The starch containing material may e.g. be selected from the groups consisting of corns, cobs, wheat, barley, cassava, sorghum, rye, milo and potatoes; or any combination of the forgoing.

In the ethanol processes of the invention, the starting raw material is preferably whole grain or at least mainly whole grain. A wide variety of starch containing whole grain crops may be used as raw material including: corn (maize), milo, potato, cassava, sorghum, wheat, and barley.

Thus, in one embodiment, the starch containing material is whole grain selected from the group consisting of corn (maize), milo, potato, cassava, sorghum, wheat, and barley; or any combinations thereof. In a preferred embodiment, the starch containing material is whole grain selected from the group consisting of corn, wheat and barley or any combinations thereof.

The raw material may also consist of or comprise a side stream from starch processing—e.g. C6 carbohydrate containing process streams that are not suited for production of syrups. In other embodiments, the raw material does not consist of or comprise a side stream from starch processing.

Process Steps

The main process steps of the present invention may in one embodiment be described as separated into the following main process stages: milling (when whole grain is used as raw material), primary liquefaction, heat-treatment as provided by jet-cooking, secondary liquefaction, saccharification, fermentation, distillation.

In a preferred embodiment, the method of the invention comprises prior to step (a) the steps of: i) dry milling of whole grain; and ii) forming a slurry comprising the milled grain and water.

The individual process steps of alcohol production may be performed batch wise or as a continuous flow. For the invention processes where all process steps are performed batch wise, or processes where all process steps are performed as a continuous flow, or processes where one or more process step(s) is(are) performed batch wise and one or more process step(s) is(are) performed as a continuous flow, are equally contemplated.

The cascade process is an example of a process where one or more process step(s) is(are) performed as a continuous flow and as such contemplated for the invention. For further information on the cascade process and other ethanol processes consult The Alcohol Textbook. Ethanol production by fermentation and distillation. Eds. T. P. Lyons, D. R. Kesall and J. E. Murtagh. Nottingham University Press 1995.

Milling

Thus, in a preferred embodiment of the process of the invention, the starch containing material is whole grain and the method comprises a step of milling the whole grain before step (a), i.e. before the primary liquefaction. In other words, the invention also encompasses processes of the invention, wherein the starch containing material is obtainable by a process comprising milling of whole grain, preferably dry milling, e.g. by hammer or roller mils.

Grinding is also Understood as Milling.

In particular embodiments, the process of the invention further comprises prior to the primary liquefaction step (i.e. prior to step (a), the steps of:
  i. milling of whole grain;
  ii. forming a slurry comprising the milled grain and water to obtain the starch containing material.

The whole grain is milled in order to open up the structure and allowing for further processing. Two processes of milling are normally used in alcohol production: wet and dry milling. The term "dry milling" denotes milling of the whole grain. In dry milling the whole kernel is milled and used in the remaining part of the process. Wet milling gives a good separation of germ and meal (starch granules and protein) and is with a few exceptions applied at locations where there is a parallel production of syrups.

Thus, in a preferred embodiment of the invention, dry milling is used since the secondary liquefaction step is advantageously included in dry milling processes for producing ethanol.

Liquefaction

In the liquefaction process the starch containing material, preferably in the form of milled whole grain raw material is broken down (hydrolyzed) into maltodextrins (dextrins). In a preferred embodiment, in the primary liquefaction process of the invention the starch containing material, preferably in the form of milled whole grain raw material, is hydrolyzed to a DE (an abbreviation for dextrose equivalent) higher than 4. DE stands for "Dextrose equivalents" and is a measure of reducing ends on C6 carbohydrates. Pure glucose has DE of 100. Glucose (also called dextrose) is a reducing sugar. Whenever an amylase hydrolyzes a glucose-glucose bond in starch, two new glucose end-groups are exposed. At least one of these can act as a reducing sugar. Therefore the degree of hydrolysis can be measured as an increase in reducing sugars. The value obtained is compared to a standard curve based on pure glucose—hence the term dextrose equivalent. The DE may, e.g., be measured using Fehlings liquid by forming a copper complex with the starch using pure glucose as a reference, which subsequently is quantified through iodometric titration. In other words: DE (dextrose equivalent is defined as the amount of reducing carbohydrate (measured as dextrose-equivalents) in a sample expressed as w/w % of the total amount of dissolved dry matter. It may also be measured by the neocuproine assay (Dygert, Li Floridana (1965) Anal. Biochem. No 368). The principle of the neocuproine assay is that $CuSO_4$ is added to the sample, $Cu^{2+}$ is reduced by the reducing sugar and the formed neocuproine complex is measured at 450 nm.

The hydrolysis may be carried out by acid treatment or enzymatically. The liquefaction, is preferably carried out by enzymatic treatment, preferably an alpha-amylase treatment. In one embodiment, the liquefaction is carried out by preparing a slurry comprising milled raw material, preferably milled whole grain, and water, heating the slurry to between 60–95° C., preferably 80–85° C., and the enzyme(s) is (are) added to initiate liquefaction (thinning). This is also termed the "primary liquefaction", i.e. it occurs before the process step of jet-cooking (step (b)). The liquefaction in the process of the invention is performed at any conditions i.e. e.g. pH, temperature and time) found suitable for the enzyme in question. Within the scope is a method of the invention, wherein the liquefaction in step (a) is performed at 60–95° C. for 10–120 min, preferably at 75–90° C. for 15–40 min. In one embodiment, the liquefaction in step (a) is performed at a pH in the range of about pH 4–7, preferably pH about 4.5–6.5. The pH of the slurry may by adjusted or not, depending on the properties of the enzyme(s) used. Thus, in one embodiment the pH is adjusted, e.g. about 1 unit upwards, e.g. by adding NH3. The adjusting of pH is advantageously done at the time when the alpha-amylase is added. In a preferred embodiment, the pH is not adjusted and the alpha-amylase has a corresponding suitable pH-activity profile, such as being active at a pH about 4.

After the primary liquefaction step, the slurry is preferably jet-cooked at appropriate conditions to further gelatinize the starch, such as, e.g. at a temperature between 95–140° C., preferably 105–125° C. to ensure the gelanitization. In one embodiment, the jet-cooking in step (b) is performed under conditions 1–10 min, 105–150° C. and e.g. pH 4–7; preferably for 1–5 min, 105–120° C. and e.g. pH 4.5–6; such as, e.g., about 5 min, about 105° C., and e.g. pH about 5.0. As used herein, generally, the term jet-cooking also covers any other method which can be used to obtain a similar result.

Then the slurry is preferably cooled, e.g. to about 60–95° C. and more enzyme(s) is (are) added to obtain the final hydrolysis; the later is termed "secondary liquefaction", i.e. liquefaction after jet-cooking which by the process of the invention is obtained by addition of at least a thermostable acid alpha-amylase or a thermostable maltogenic acid alpha-amylase.

The secondary liquefaction in step (c) is performed at suitable conditions (pH, temperature and process time). The secondary liquefaction in step (c) may e.g., be performed at 60–95° C. for 10–120 min, preferably at 70–85° C. for 15–80 min and at pH 4.5–6.5. In one embodiment, the pH is not adjusted for the secondary liquefaction. In preferred embodiment, the pH during the secondary liquefaction is at most about 5.

In one preferred embodiment, in the secondary liquefaction step in the method of the invention the starch containing material, e.g. obtained from dry milled whole grain, is hydrolyzed to a DE in the range of about 5–15, e.g. 8–15, 8–14, such as, such as a DE in the range about 10–14., e.g. about 10–12.

The liquefaction process (both the primary and the secondary liquefaction process) is carried out at a suitable pH, e.g. at a pH In the range 4.5–6.5, such as at a pH between about 5 and about 6.

Milled and liquefied whole grain are also known as mash.

Saccharification

To produce low molecular sugars $DP_{1-2}$ that can be metabolized by yeast, the maltodextrin from the liquefaction is preferably further hydrolyzed; this is also termed "saccharification". The hydrolysis may by done enzymatically by the presence of a glucoamylase. An alpha-glucosidase and/or an acid alpha-amylase may also be present in addition to the glucoamylase.

A full saccharification step may last up to 72 hours. However, the saccharification and fermentation (SSF) may be combined, and in some embodiments of the invention a pre-saccharification step of 1–4 hours may be included. Pre-saccharification is carried out at any suitable process conditions. In a preferred embodiment, the pre-saccharification is carried out at temperatures from 30–65° C., such as around 60° C., and at, e.g., a pH in the range between 4–5, especially around pH 4.5.

Thus in one embodiment, the method of the invention may further comprise a pre-saccharification step, as described herein, which is performed after the secondary liquefaction step (c) and before step (d).

In other embodiments, the process of the invention does not comprise a pre-saccharification and the saccharification is essentially only performed during fermentation, e.g. by the presence of a glucoamylase and optionally phytase.

Fermentation

The microorganism used for the fermentation is added to the mash and the fermentation is ongoing until the desired amount of ethanol is produced; this may, e.g., be for 24–96 hours, such as 35–60 hours. The temperature and pH during fermentation is at a temperature and pH suitable for the microorganism in question, such as, e.g., in the range about 26–34° C., e.g. about 32° C., and at a pH e.g. in the range about pH 3–6, e.g. about pH 4–5.

In a preferred embodiment, a simultaneous saccharification and fermentation (SSF) process is employed where there is no holding stage for the saccharification, meaning that yeast and saccharification enzyme is added essentially together. In one embodiment, when doing SSF is introduced a pre-saccharification step at a temperature above 50° C., just prior to the fermentation.

In one embodiment, the fermentation is carried out in the presence of glucoamylase and/or protease.

In a further embodiment, the addition of a thermostable acid alpha-amylase or a thermostable maltogenic acid alpha-amylase in the secondary liquefaction step in the process of the invention may make it possible to substitute the presence of glucoamylase activity in the fermentation step. Thus, one embodiment relates to a process of the invention for the production of ethanol, without addition of glucoamylase in the fermentation step or prior to the fermentation step.

Distillation

The method of the invention may further comprise recovering of the ethanol; hence the alcohol may be separated from the fermented material and purified. Following the fermentation the mash may be distilled to extract the ethanol. Ethanol with a purity of up to e.g. about 96 vol. % ethanol can be obtained by the process of the invention.

Thus, in one embodiment, the method of the invention further comprises the step of: (e) distillation to obtain the ethanol. The fermentation in step (d) and the distillation in step (e) may be carried out simultaneously and/or separately/sequentially; optionally followed by one or more process steps for further refinement of the ethanol.

By-products from Distillation and Recycling:

In one embodiment of the process of the invention, the aqueous by-product ("Whole Stillage", cf. FIG. 1) from the distillation process is separated into two fractions, for instance by centrifugation: 1) "Wet Grain" (solid phase, see FIG. 1), and 2) "Thin Stillage" (Supernatant, see FIG. 1).

In one embodiment, the starch containing material entering the process of the invention is dry milled whole grain, and the method of the invention comprising steps (a), (b), (c), (d), and (e) further comprises the steps of:
(f) separation of Whole Stillage produced by of the distillation in step (e), into wet grain and Thin stillage; and
(g) recycling Thin stillage to the starch containing material prior to the primary liquefaction of step (a).

In one embodiment, in the process of the invention, the Thin Stillage (cf. FIG. 1) is recycled to the milled whole grain slurry.

The Wet Grain fraction may be dried, typically in a drum dryer. The dried product is referred to as "Distillers Dried Grains" (see FIG. 1), and can be used, e.g., as animal feed.

The Thin Stillage fraction may be evaporated providing two fractions (see FIG. 1):
(i) a Condensate fraction of 4–6% DS (mainly of starch, proteins, and cell wall components), and
(ii) a Syrup fraction, mainly consisting of limit dextrins and non fermentable sugars, which may be introduced into a dryer together with the Wet Grains (from the Whole Stillage separation step) to provide a product referred to as "Distillers Dried Grain", which also can be used as animal feed.

"Thin Stillage" is the term used for the supernatant of the centrifugation of the Whole Stillage (see FIG. 1). Typically, the Thin Stillage contains 4–6% DS (mainly starch and proteins) and has a temperature of about 60–90° C.

In another embodiment Thin Stillage is not recycled, but the condensate stream of evaporated Thin Stillage is recycled to the slurry containing the milled whole grain to be jet cooked.

One embodiment of the invention relates to a method of producing ethanol, said method comprising the steps of:
a) primary liquefaction of a starch containing material in the presence of alpha-amylase activity;
b) jet cooking the material of step(a);
c) secondary liquefaction of the material of step (b) in the presence of a thermostable acid alpha-amylase or, a thermostable maltogenic acid alpha-amylase; and
d) saccharification and fermentation to produce ethanol;

wherein the steps (a), (b), (c) and (d) is performed in the order (a), (b), (c), (d).

Optionally the saccharification and fermentation may be performed in separate steps. Thus the invention also relates to a method of producing ethanol, said method comprising the steps of:
a) primary liquefaction of a starch containing material in the presence of alpha-amylase activity;
b) jet cooking the material of step(a);
c) secondary liquefaction of the material of step (b) in the presence of a thermostable acid alpha-amylase or, a thermostable maltogenic acid alpha-amylase; and
d) saccharification;
e) fermentation to produce ethanol;

wherein the steps (a), (b), (c) and (d) is performed in the order (a), (b), (c), (d) and wherein (e) is performed simultaneously to or following (d).

The invention in also relates to a method of producing ethanol, said method comprising the steps of:
a) dry milling of whole grain;
b) forming a slurry comprising the milled grain and water;
c) liquefaction in the presence of an alpha-amylase;
d) jet cooking;
e) liquefaction in the presence of a thermostable acid alpha-amylase or a thermostable maltogenic acid alpha-amylase;
f) saccharification in the presence of phytase and/or glucoamylase and fermentation to produce ethanol;
g) distillation;

optionally followed by one or more process steps for further refinement of the ethanol;

wherein the steps(a), (b), (c), (d), (e) and (f) is performed in the order (a), (b), (c), (d), (e), (f); and wherein step (g) is performed simultaneously with step (f) and/or after step (f).

In a further embodiment, the method of the invention for producing ethanol may comprise the following steps:
a) milling whole grain;
b) making a slurry comprising the milled whole grain and water;
c) liquefying in the presence of an alpha-amylase;
d) saccharifying in the presence of a glucoamylase and fermenting using a microorganism;
f) distillation of the fermented material, providing two streams 1) alcohol and 2) Whole Stillage;
(g1) recovering alcohol for further refinement; optionally,
(g2) separating the Whole Stillage into two fractions of: 1) Wet Grain, and 2) Thin Stillage;
(h1) the whole grain fraction is dried to provide a protein containing product, and optionally
(h2) the Thin Stillage is evaporated providing two streams: 1) condensate stream and 2) syrup;

wherein the Thin Stillage and optionally the condensate from step (h2) is recycled to step (b) with or without further treatment.

Enzyme Activities

Alpha-amylase

The "primary liquefaction" is preferably performed in the presence of an alpha-amylase, e.g., derived from a microorganism or a plant. Preferred alpha-amylases are of fungal or bacterial origin. *Bacillus* alpha-amylases (often referred to as "Termamyl-like alpha-amylases"), variant and hybrids thereof, are specifically contemplated according to the invention. Well-known Termamyl-like alpha-amylases include alpha-amylase derived from a strain of *B. licheniformis* (commercially available as Termamyl™), *B. amyloliquefaciens*, and *B. stearothermophilus* alpha-amylase. Other Termamyl-like alpha-amylases include alpha-amylase derived from a strain of the *Bacillus* sp. NCIB 12289, NCIB 12512, NCIB 12513 or DSM 9375, all of which are described in detail in WO 95/26397, and the alpha-amylase described by Tsukamoto et al., Biochemical and Biophysical Research Communications, 151 (1988), pp. 25–31. In the context of the present invention a Termamyl-like alpha-amylase is an alpha-amylase as defined in WO 99/19467 on page 3, line 18 to page 6, line 27. Contemplated variants and hybrids are described in WO 96/23874, WO 97/41213, and WO 99/19467, and include the *Bacillus stearothermophilus* alpha-amylase (BSG alpha-amylase) variant, alpha-amylase TTC, having the following mutations delta(181–182)+N193F (also denoted I181*+G182*+N193F) compared to the wildtype amino acid sequence set forth in SEQ ID NO:3 disclosed in WO 99/19467. Contemplated alpha-amylase derived from a strain of *Aspergillus* includes *Aspergillus oryzae* and *Aspergillus niger* alpha-amylases.

Commercial alpha-amylase products and products containing alpha-amylases include TERMAMYL™ SC, FUNGAMYL™, LIQUOZYME™ SC and SAN™ SUPER, (Novozymes A/S, Denmark) and DEX-LO™, SPEZYME™ AA, and SPEZYME™ DELTA AA (from Genencor Int.)

Other contemplated alpha-amylase is the KSM-K36 alpha-amylase disclosed in EP 1,022,334 and deposited as FERM BP 6945, and the KSM-K38 alpha-amylases disclosed in EP 1,022,334, and deposited as FERM BP-6946. Also variants therefore are contemplated, in particular the variants disclosed in Danish patent application no. PA 2000 11533 (from Novozymes A/S.

The "secondary liquefaction" is performed in the presence of an alpha-amylase, in particular a thermostable acid alpha-amylase or a thermostable maltogenic acid alpha-amylase as described herein for use in the secondary liquefaction step in the process of the invention. The alpha-amylase is preferably derived from a micro-organism, including fungal and bacterial, or derived from a plant. Preferred thermostable acid alpha-amylases are of bacterial origin. Prefered thermostable maltogenic acid alpha-amylase are of fungal origin.

It is understood that enzymes are added in an effective amount for the actual conditions (temperature, pH) of the process, e.g. that the thermostable acid alpha-amylase is added in an amount effective in step (c).

In further embodiments of the process of the invention, in step (c) apart from the addition of the thermostable acid alpha-amylase is also added an alpha-amylase which is not a thermostable acid alpha-amylase.

The term "thermostable" in the context of a thermostable acid alpha-amylase means in one embodiment that the enzyme is active up to 90° C. at pH 5.0 using a 0.1 M citrate buffer and 4.3 mM $Ca^{2+}$.

The thermostable acid alpha-amylase should have activity at the pH present during the liquefaction and fermentation, such as e.g. at a pH in the range pH 2.5–5.5 using a 0.1 M citrate buffer and 4.3 mM $Ca^{2+}$. The enzyme should preferably at least be active in the range at pH 3–5. It is understood that the enzyme may also be active outside the pH ranges mentioned.

Examples of thermostable acid alpha-amylases as used herein are the alpha-amylase selected from the group consisting of LE399; the *Aspergillus oryzae* TAKA alpha-amylase (EP 238 023); the *Aspergillus niger* alpha-amylase disclosed in EP 383,779 B2 (section [0037] (see also the cloning of the *A. niger* gene in Example 1); the *Aspergillus niger* alpha-amylase disclosed in Example 1 of EP 140,410;

Commercial fungal alpha-amylases FUNGAMYL® (Novozymes A/S); and Clarase™ (from Genencor Int., USA), the later both derived from *Aspergillus*.

LE399 is a hybrid alpha-amylase. Specifically, LE399 comprises the 445 C-terminal amino acid residues of the *Bacillus licheniformis* alpha-amylase (shown in SEQ ID NO: 4 of WO 99/19467) and the 37 N-terminal amino acid residues of the alpha-amylase derived from *Bacillus amyloliquefaciens* (shown in SEQ ID NO: 5 of WO 99/19467), with the following substitution: G48A+T49I+G107A+ H156Y+A181T+N190F+I201F+A209V+Q264S (using the numbering in SEQ ID NO: 4 of WO 99/19467).

By the expression "secondary liquefaction in the presence of a thermostable acid alpha-amylase" is understood liquefaction in the secondary liquefaction step in the process of the invention by treatment with an effective amount of a thermostable acid alpha-amylase" as defined herein.

The thermal/pH stability may be tested using, e.g., the following method: 950 micro liter 0.1 M Citrate+4.3 mM $Ca^{2+}$ buffer is incubated for 1 hour at 60° C. 50 micro liter enzyme in buffer (4 AFAU/ml) is added. 2×40 micro liter samples are taken at 0 and 60 minutes and chilled on ice. The activity (AFAU/ml) measured before incubation (0 minutes) is used as reference (100%). The decline in percent is calculated as a function of the incubation time. To determine the Thermal stability the test is repeated using different temperatures, for instance 50, 60, 70, 80 and 90° C. To determine the pH stability the test is repeated using different pH's, for instance, pH 2.5; 3; 3.5; 4; 4.5; 5.

An examples of an alpha-amylase, in particular a thermostable maltogenic acid alpha-amylase, used in the process of the invention is the alpha-amylase having the amino acid sequence set forth in SEQ ID NO:1 (also named SP288) and variants thereof having one or more amino acid residues which have been deleted, substituted and/or inserted compared to the amino acid sequence of SEQ ID NO:1; which variants have alpha-amylase activity, preferably being a thermostable maltogenic acid alpha-amylase.

Thus, the alpha-amylase used in the secondary liquefaction step in the process of the invention, may e.g. be an alpha-amylase, in particular a thermostable maltogenic acid alpha-amylase, having an amino acid sequence which has at least 70% identity to SEQ ID NO:1 preferably at least 75%, 80%, 85% or at least 90%, e.g. at least 95%, 97%, 98%, or at least 99% identity to SEQ ID NO:1. In the present context, the degree of identity between two amino acid sequences is described by the parameter "identity" given in %. For purposes of the present invention, the degree of identity between two amino acid sequences is preferably determined by the Clustal method (Higgins, 1989, CABIOS 5: 151–153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters were Ktuple=1, gap penalty=3, windows=5, and diagonals=5].

Thus, the thermostable maltogenic acid alpha-amylase used in the process of the invention may e.g. also be an alpha-amylase, in particular a thermostable maltogenic acid alpha-amylase, having an amino acid sequence which is a fragment of SEQ ID NO 1. When using the term "alpha-amylase" or "thermostable maltogenic acid alpha-amylase" in the context of variants and fragments of e.g. SEQ ID NO:1, it is to be understood that the enzyme is capable of being enzymatically active. When used herein, a "fragment" of SEQ ID NO:1 is a polypeptide having one or more amino acids deleted from the amino and/or carboxyl terminus of this amino acid sequence. Preferably, a fragment contains at least 50 amino acid residues or at least 100 amino acid residues.

The enzyme given by SEQ ID NO:1 is also disclosed in Boel E. et al: "Calcium binding in alpha-amylases: an X-ray diffraction study at 2.1-Å resolution of two enzymes from *Aspergillus*". Biochemistry, 29:6244–6249, Publ. Year: 1990, e.g. in table 1 and under "Material and Methods" of the same.

Other examples of alpha-amylases which may be used in the secondary liquefaction step in the process of the invention, is the alpha-amylase disclosed in Agric. Biol. Chem., 43:1165–1171, 1979 by Guy-Jean Moulin and Pierre Galzy.

It is understood that the enzyme are added in an effective amount for the actual conditions (temperature, pH) of the process, e.g. that the thermostable maltogenic acid alpha-amylase is added in an amount effective in step (c).

In further embodiments of the process of the invention, in the secondary liquefaction step (c) apart from the addition of a thermostable maltogenic acid alpha-amylase (e.g. the alpha-amylase of SEQ ID NO:1 and variants thereof as described herein) is also added an alpha-amylase which is not a thermostable maltogenic acid alpha-amylase as defined herein, such as e.g. the alpha-amylase TTC.

The thermostable maltogenic acid alpha-amylase should have activity at the pH present during the liquefaction and fermentation; such as e.g. at a pH in the range pH 2.5–5.5 using a 0.1 M citrate buffer and 4.3 mM $Ca^{2+}$, a substrate consisting of DE 12 alpha-amylase TTC liquefied corn starch at 30% dry substance. The enzyme should preferably at least be active in the range at pH 3–5, preferably at least pH 2.5–5. It is understood that the enzyme may also be active outside the pH ranges mentioned.

The term "maltogenic" in the context of the invention, means that the enzyme is capable of releasing a relatively high amount of α-maltose as a product of its enzymatic activity.

In a particular interesting embodiment, the term "maltogenic" means that the enzyme using a DE 12 alpha-amylase TTC liquefied corn starch at 30% dry substance at 60° C., pH 4.5 and dosing the enzyme at 1 AFAU/g dry substance, the enzyme will in 24 hours catalyze the formation of at least 15%, or at least 20%, at least 25%, at least 30 w/w maltose as based on the total amount of starch. The maltose content may for instance by measured by with HPLC as known by the person skilled in the art.

The term "DE 12 alpha-amylase TTC liquefied corn starch" in this context means that the substrate used for testing the maltogenisity of the alpha-amylase enzyme, is corn starch liquefied to a DE of 12 with alpha-amylase TTC.

The term "thermostable" means that the enzyme is relatively stable at higher temperatures. In one embodiment, the enzyme will maintain more than 90% of its activity for 1 hour at 70° C. using a DE 12 alpha-amylase TTC liquefied corn starch at 30% dry substance as substrate, pH 5.5, 0.1 M citrate buffer and 4.3 mM $Ca^{2+}$.

The term "acid" means that the enzyme is relatively stable at low pH. In one embodiment, the enzyme will maintain more than 70% of its activity in the range from pH 3.5–5.0 (e.g. at pH 4), or preferably in the range from pH 3.8–4.7 (e.g. at pH 4.2) at the conditions: substrate DE 12 alpha-amylase TTC liquefied corn starch at 30% dry substance, Temperature 40° C., and 0.1 M citrate buffer and 4.3 mM $Ca^{2+}$.

In one embodiment, the pH window (profile) of the enzyme used in the secondary liquefaction step in the process of the invention is as follows: the maximum activity of the enzyme is found at approximately pH 4.2 and/or the enzyme will maintain more than 70% of its activity in the range from pH 3.5–5.0 at the conditions: substrate is DE 12 alpha-amylase TTC liquefied corn starch at 30% dry substance, Temperature 40° C., and 0.1 M citrate buffer and 4.3 mM $Ca^{2+}$.

In one embodiment, the temperature window (profile) of the alpha-amylase enzyme used in the secondary liquefaction step in the process of the invention is as follows: the enzyme will maintain more than 80% of its activity for 15 min in the range from 50–80° C. using a DE 12 alpha-amylase TTC liquefied corn starch at 30% dry substance as substrate. pH 5.5, 0.1 M citrate buffer and 4.3 mM $Ca^{2+}$.

The alpha-amylase enzyme used in the secondary liquefaction step in the process of the invention may catalyse the hydrolysis of beta-cyclodextrins which is one of the characteristics of the enzyme having the amino acid sequence of SEQ ID NO:1.

By the expression "secondary liquefaction in the presence of a thermostable maltogenic acid alpha-amylase" is understood liquefaction in the secondary liquefaction step by treatment with an effective amount of a thermostable maltogenic acid alpha-amylase" as defined herein. The alpha-amylase used in the secondary liquefaction is preferably a thermostable maltogenic acid alpha-amylase. The term "thermostable maltogenic acid" alpha-amylase", means that the alpha-amylase is both thermostable, acid and maltogenic as defined herein. In one embodiment, the alpha-amylase is at least thermostable and acid as defined herein, optionally being maltogenic as defined herein.

The thermostable maltogenic acid alpha-amylase may be employed in the primary liquefaction step; however, the maximum effect is obtained if the enzyme is added the secondary liquefaction step.

Enzyme Activities Used During Saccharification or SSF

Glucoamylase

The saccharification step or the simultaneous saccharification and fermentation step (SSF) may be carried out in the presence of a glucoamylase. The glucoamylase may be of any origin., e.g. derived from a microorganism or a plant. Preferred is glucoamylase of fungal or bacterial origin selected from the group consisting of *Aspergillus niger* glucoamylase, in particular *A. niger* G1 or G2 glucoamylase (Boel et al. (1984), EMBO J. 3 (5), p. 1097–1102), or variants thereof, such as disclosed in WO 92/00381 and WO 00/04136; the *A. awamori* glucoamylase (WO 84/02921), *A. oryzae* (Agric. Biol. Chem. (1991), 55 (4), p. 941–949), or variants or fragments thereof.

Other contemplated *Aspergillus* glucoamylase variants include variants to enhance the thermal stability: G137A and G139A (Chen et al. (1996), Prot. Engng. 9, 499–505); D257E and D293E/Q (Chen et al. (1995), Prot. Engng. 8, 575–582); N182 (Chen et al. (1994), Biochem. J. 301, 275–281); disulphide bonds, A246C (Fierobe et al. (1996), Biochemistry, 35, 8698–8704; and introduction of Pro residues in position A435 and S436 (Li et al. (1997), Protein Engng. 10, 1199–1204. Furthermore, Clark Ford presented a paper on Oct. 17, 1997, ENZYME ENGINEERING 14, Beijing/China Oct. 12–17, 1997, Abstract number: Abstract book p. 0–61. The abstract suggests mutations in positions G137A, N20C/A27C, and S30P in an *Aspergillus awamori* glucoamylase to improve the thermal stability. Other glucoamylases include *Talaromyces* glucoamylases, in particular derived from *Talaromyces emersonii* (WO 99/28448), *Talaromyces leycettanus* (U.S. Pat. No. Re. 32,153), *Talaromyces duponti*, *Talaromyces thermopiles* (U.S. Pat. No. 4,587,215). Bacterial glucoamylases contemplated include glucoamylases from the genus *Clostridium*, in particular *C. thermoamylolyticum* (EP 135,138), and *C. thermohydrosulfuricum* (WO 86/01831).

Commercial products include SAN™ SUPER™ and AMG™ E (from Novozymes A/S).

Protease

Addition of protease(s) In the saccharification step, the SSF step and/or the fermentation step increase(s) the FAN (Free amino nitrogen) level and increase the rate of metabolism of the yeast and further gives higher fermentation efficiency.

Suitable proteases include microbial proteases, such as fungal and bacterial proteases. Preferred proteases are acidic proteases, i.e., proteases characterized by the ability to hydrolyze proteins under acidic conditions below pH 7.

In a preferred embodiment, the protease is selected from the group of fungal proteases, such as e.g. an acid fungal protease derived from a strain of *Aspergillus*.

Suitable acid fungal proteases include fungal proteases derived from *Aspergillus, Mucor, Rhizopus, Candida, Coriolus, Endothia, Enthomophtra, Irpex, Penicillium, Sclerotium* and *Torulpsis*. Especially contemplated are proteases derived from *Aspergillus niger* (see, e.g., Koaze et al., (1964), Agr. Biol. Chem. Japan, 28, 216), *Aspergillus saitoi* (see, e.g., Yoshida, (1954) J. Agr. Chem. Soc. Japan, 28, 66), *Aspergillus awamori* (Hayashida et al., (1977) Agric. Biol. Chem., 42(5), 927–933, *Aspergillus aculeatus* (WO 95/02044), or *Aspergillus oryzae*, such as the pepA protease; and acidic proteases from *Mucor pusillus* or *Mucor miehei*.

Also contemplated are neutral or alkaline proteases, such as a protease derived from a strain of *Bacillus*. Bacterial proteases, which are not acidic proteases, include the commercially available products Alcalase® and Neutrase® (available from Novozymes A/S.

Additional Enzymes:

One or more additional enzymes may also be used during saccharification/pre-saccharification or SSF. Additional enzymes include e.g. pullulanase and/or phytase. Thus, in one embodiment, is added a glucoamylase and/or phytase in order to promote the fermentation.

Phytase:

The phytase used according to the invention may be any enzyme capable of effecting the liberation of inorganic phosphate from phytic acid (myo-inositol hexakisphosphate) or from any salt thereof (phytates). Phytases can be classified according to their specificity in the initial hydrolysis step, viz. according to which phosphate-ester group is hydrolyzed first. The phytase to be used in the invention may have any phytase specificity, e.g., be a 3-phytase (EC 3.1.3.8), a 6-phytase (EC 3.1.3.26) or a 5-phytase.

A suitable dosage of the phytase is e.g. in the range 5.000–250.000 FYT/g DS, particularly 10.000–100.000 FYT/g DS.

The phytase activity may be determined FYT units, one FYT being the amount of enzyme that liberates 1 micromole inorganic ortho-phosphate per min. under the following conditions: pH 5.5; temperature 37° C.; substrate: sodium phytate ($C_6H_6O_{24}P_6Na_{12}$) at a concentration of 0.0050 mole/l.

The phytase may be of any origin, such as, e.g. microbial, such as, e.g., derived from a strain of *Peniophra lycii* or *Aspergillus oryzae*. It may be produced recombinantely or non-recobinantly. The phytase may be derived e.g. from plants or microorganisms, such as bacteria or fungi, e.g., yeast or filamentous fungi.

The plant phytase may be from wheat-bran, maize, soy bean or lily pollen. Suitable plant phytases are described in Thomlinson et al, Biochemistry, 1 (1962), 166–171; Barrientos et al, Plant. Physiol., 106 (1994), 1489–1495; WO 98/05785; WO 98/20139.

A bacterial phytase may be from genus *Bacillus, Pseudomonas* or *Escherichia*, specifically the species *B. subtilis* or *E coli*. Suitable bacterial phytases are described in Paver and Jagannathan, 1982, Journal of Bacteriology 151: 1102–1108; Cosgrove, 1970, Australian Journal of Biological Sciences 23:1207–1220; Greiner et al, Arch. Biochem. Biophys., 303, 107–113, 1993; WO 98/06856; WO 97/33976; WO 97/48812.

A yeast phytase or myo-inositol monophosphatase may be derived from genus *Saccharomyces* or *Schwanniomyces*, specifically species *Saccharomyces cerevisiae* or *Schwanniomyces occidentalis*. The former enzyme has been described as a Suitable yeast phytases are described in Nayini et al, 1984, Lebensmittel Wissenschaft und Technologie 17:24–26; Wodzinski et al, Adv. Appl. Microbiol., 42, 263–303; AU-A-24840/95;

Phytases from filamentous fungi may be derived from the fungal phylum of Ascomycota (ascomycetes) or the phylum Basidiomycota, e.g., the genus *Aspergillus, Thermomyces* (also called *Humicola*), *Myceliophthora, Manascus, Penicillium, Peniophora, Agrocybe, Paxillus*, or *Trametes*, specifically the species *Aspergillus terreus, Aspergillus niger, Aspergillus niger* var. *awamori, Aspergillus ficuum, T. lanuginosus* (also known as *H. lanuginosa*), *Myceliophthora thermophila, Peniophora lycii, Agrocybe pediades, Manascus anka, Paxillus involtus*, or *Trametes pubescens*. Suitable fungal phytases are described in Yamada et al., 1986, Agric. Biol. Chem. 322:1275–1282; Piddington et al., 1993, Gene 133:55–62; EP 684,313; EP 0 420 358; EP 0 684 313; WO 98/28408; WO 98/28409; JP 7-67635; WO 98/44125; WO 97/38096; WO 98/13480.

Modified phytases or phytase variants are obtainable by methods known in the art, in particular by the methods disclosed in EP 897010; EP 897985; WO 99/49022; WO 99/48330.

Microorganism Used for Fermentation

Preferably microorganisms are used for the fermentation in step (d). The microorganism may be a fungal organism, such as yeast, or bacteria. Suitable bacteria may e.g. be *Zymomonas* species, such as *Zymomonas mobilis* and *E. coli*. Examples of filamentous fungi include strains of *Penicillium* species. Preferred organisms for ethanol production are yeasts, such as e.g. *Pichia* or *Saccharomyces*. Preferred yeast according to the invention is *Saccharomyces* species, in particular *Saccharomyces cerevisiae* or bakers yeast.

Use of the Products Produced by the Method of the Invention

The ethanol obtained by the process of the invention may be used as, e.g., fuel ethanol; drinking ethanol, i.e., potable neutral spirits, or industrial ethanol, including fuel additive.

The invention in further aspect relates to use of a thermostable acid alpha-amylase or a thermostable maltogenic acid alpha-amylase in the secondary liquefaction step in a process for production of ethanol; included is use of a thermostable acid alpha-amylase or a thermostable maltogenic acid alpha-amylase in the secondary liquefaction step in the processes of the invention disclosed herein.

Advantages of the Process of the Invention

By employing the thermostable acid alpha amylase of the invention in the secondary liquefaction step, the process of the invention provides an improved process of producing ethanol. By the process of the invention the overall yield and/or process economy is increased. The process of the invention may make possible a lowering of the fermentation time. Further, the process of the invention may enhance the fermentation efficiency, e.g. by reducing the residual starch otherwise left over in the fermentation. Furthermore, the process of the invention may reduce or eliminate the need for a pre-saccharification step.

By employing the thermostable maltogenic acid alpha amylase of the invention in the secondary liquefaction step, the process of the invention provides an improved process of producing ethanol. By the process of the invention the overall yield and/or process economy is increased. The described thermostable maltogenic acid alpha-amylase will, when used in the secondary liquefaction, produce a higher number of fermentable sugars (maltose) as compared to the non-maltogenic alpha-amylases presently employed. This reduces the fermentation time and/or the dosage of glucoamylase enzyme which is required to form fermentable sugars. Also as molecules of a lower molecular weight are formed the viscosity will be reduced as compared to non-maltogenic alpha-amylases. Reduced viscosity is desired in e.g. heat exchangers and dryers. Furthermore, the thermostable maltogenic acid alpha-amylase by being active during fermentation conditions, and since this enzyme has an endo-breakdown mechanism it will in combination with the glucoamylase which is an exo-enzyme enable a more efficient hydrolysis of the starch during fermentation. Thus the process of the invention may make possible a lowering of the fermentation time. The process of the invention may enhance the fermentation efficiency, e.g. by reducing the residual starch otherwise left over in the fermentation. Furthermore, the process of the invention may reduce or eliminate the need for a pre-saccharification step.

Material & Methods

Determination of Viscosity

The mash is heated to a temperature of 50–70° C., depending on the treatment. Following treatment viscosity is measured using a Haake VT02 rotation based viscosimeter. The unit of viscosity is centipois (cps), which is proportionally related to the viscosity level.

Determination of Alpha-Amylase Activity (KNU)

The KNU is used to measure bacterial alpha-amylases with a high pH optima.

Phadebas Assay

Alpha-amylase activity is determined by a method employing Phadebas® tablets as substrate. Phadebas tablets (Phadebas® Amylase Test, supplied by Pharmacia Diagnostic) contain a cross-linked insoluble blue-colored starch polymer, which has been mixed with bovine serum albumin and a buffer substance and tabletted.

For every single measurement one tablet is suspended in a tube containing 5 ml 50 mM Britton-Robinson buffer (50 mM acetic acid, 50 mM phosphoric acid, 50 mM boric acid, 0.1 mM $CaCl_2$, pH adjusted to the value of interest with NaOH). The test is performed in a water bath at the temperature of interest. The alpha-amylase to be tested is diluted in x ml of 50 mM Britton-Robinson buffer. 1 ml of this alpha-amylase solution is added to the 5 ml 50 mM Britton-Robinson buffer. The starch is hydrolyzed by the alpha-amylase giving soluble blue fragments. The absorbance of the resulting blue solution, measured spectrophotometrically at 620 nm, is a function of the alpha-amylase activity.

It is important that the measured 620 nm absorbance after 10 or 15 minutes of incubation (testing time) is in the range of 0.2 to 2.0 absorbance units at 620 nm. In this absorbance range there is linearity between activity and absorbance (Lambert-Beer law). The dilution of the enzyme must therefore be adjusted to fit this criterion. Under a specified set of conditions (temp., pH, reaction time, buffer conditions) 1 mg of a given alpha-amylase will hydrolyze a certain amount of substrate and a blue colour will be produced. The colour intensity is measured at 620 nm. The measured absorbance is directly proportional to the specific activity (activity/mg of pure alpha-amylase protein) of the alpha-amylase in question under the given set of conditions.

Alternative Method

Alpha-amylase activity is determined by a method employing the PNP-G7 substrate. PNP-G7 which is an abbreviation for p-nitrophenyl-alpha,D-maltoheptaoside is a blocked oligosaccharide which can be cleaved by an endo-amylase. Following the cleavage, the alpha-Glucosidase included in the kit digest the substrate to liberate a free PNP molecule which has a yellow colour and thus can be measured by visible spectophometry at lambda=405 nm. (400–420 nm.). Kits containing PNP-G7 substrate and alpha-Glucosidase is manufactured by Boehringer-Mannheim (cat. No. 1054635).

To prepare the substrate one bottle of substrate (BM 1442309) is added to 5 ml buffer (BM1442309). To prepare the alpha-Glucosidase one bottle of alpha-Glucosidase (BM 1462309) is added to 45 ml buffer (BM1442309). The working solution is made by mixing 5 ml alpha-Glucosidase solution with 0.5 ml substrate.

The assay is performed by transforming 20 micro I enzyme solution to a 96 well microtitre plate and incubating at 25° C. 200 micro I working solution, 25° C. is added. The solution is mixed and pre-incubated 1 minute and absorption is measured every 15 sec. over 3 minutes at OD 405 nm.

The slope of the time dependent absorption-curve is directly proportional to the specific activity (activity per mg enzyme) of the alpha-amylase in question under the given set of conditions.

Determination of FAU Activity

One Fungal Alpha-Amylase Unit (FAU) is defined as the amount of enzyme, which breaks down 5.26 g starch (Merck Amylum solubile Erg. B.6, Batch 9947275) per hour based upon the following standard conditions:

| Substrate | Soluble starch |
|---|---|
| Temperature | 37° C. |
| pH | 4.7 |
| Reaction time | 7–20 minutes |

Determination of Acid Alpha-amylase Activity (AFAU)

Acid alpha-amylase activity is measured in AFAU (Acid Fungal Alpha-amylase Units), which are determined relative to an enzyme standard.

The standard used is AMG 300 L (from Novozymes ANS, glucoamylase wildtype *Aspergillus niger* G1, also disclosed in Boel et al. (1984), EMBO J. 3 (5), p. 1097–1102) and WO 92/00381). The neutral alpha-amylase in this AMG falls after storage at room temperature for 3 weeks from approx. 1 FAU/mL to below 0.05 FAU/mL.

The acid alpha-amylase activity in this AMG standard is determined in accordance with the following description. In this method, 1 AFAU is defined as the amount of enzyme, which degrades 5.260 mg starch dry matter per hour under standard conditions.

Iodine forms a blue complex with starch but not with its degradation products. The intensity of colour is therefore directly proportional to the concentration of starch. Amylase activity is determined using reverse colorimetry as a reduction in the concentration of starch under specified analytic conditions.

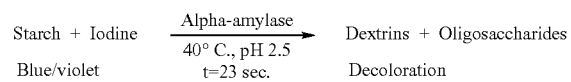

Starch + Iodine $\xrightarrow[t=23 \text{ sec.}]{\text{Alpha-amylase} \atop 40°\text{C., pH 2.5}}$ Dextrins + Oligosaccharides Blue/violet → Decoloration

| Standard conditions/reaction conditions: (per minute) | |
|---|---|
| Substrate: | Starch, approx. 0.17 g/L |
| Buffer: | Citate, approx. 0.03 M |
| Iodine ($I_2$): | 0.03 g/L |
| $CaCl_2$: | 1.85 mM |
| pH: | 2.50 ± 0.05 |
| Incubation temperature: | 40° C. |
| Reaction time: | 23 seconds |
| Wavelength: | lambda = 590 nm |
| Enzyme concentration: | 0.025 AFAU/mL |
| Enzyme working range: | 0.01–0.04 AFAU/mL |

If further details are preferred these can be found in EB-SM-0259.02/01 available on request from Novozymes A/S, and incorporated by reference.

EXAMPLES

Example 1

Secondary Liquefaction Using a Thermostable Acidic Alpha Amylase 400 mL of a ground corn slurry was liquefied by a bacterial alpha-amylase and jet cooked at 105° C. for 5 min; the resulting corn mash had 30% dry substance, DE 7 and pH 5.0. The mash was heated to 80° C. and the viscosity was measured to 500 CPS using a VT 180 viscosimeter.

The mash was treated with a thermostable acidic alpha amylase from *Aspergillus niger*. The enzyme loading was 0.25 AFAU/g of dry matter, with 1 AFAU defined as the amount of enzyme that under standard conditions (37° C., pH 2.5 in 0.01 M acetate buffer) hydrolyzes 5.25 g starch so that the hydrolyzed starch is only slightly colored by addition of iodine-potassium-iodide.

After 30 min the viscosity and DE value were measured to 350 CPS and DE 12, which shows that a final liquefaction of the corn mash was obtained.

Example 2

Secondary Liquefaction Using a Thermostable Maltogenic Acidic Alpha Amylase 400 mL of a ground corn slurry was liquefied by alpha-amylase TTC and jet cooked at 105° C. for 5 min; the resulting corn mash had 30% dry substance, DE 7 and pH 5.0. The mash was heated to 80° C. and the viscosity was measured to 500 CPS using a VT 180 viscosimeter.

The mash was treated with a thermostable maltogenic acidic alpha amylase from *Aspergillus niger* having the amino acid sequence disclosed in SEQ ID NO:1. The enzyme loading was 0.25 AFAU/g of dry matter, with 1 AFAU defined as the amount of enzyme which under standard conditions (37° C., pH 2.5 in 0.01 M acetate buffer) hydrolyzes 5.25 g starch so that the hydrolyzed starch is only slightly colored by addition of iodine-potassium-iodide.

After 30 min the viscosity and DE value were measured to 350 CPS and DE 12, which shows that a final liquefaction of the corn mash was obtained.

The invention claimed is:

1. A method of producing ethanol by fermentation comprising a secondary liquefaction step, wherein said secondary liquefaction step is carried out in the presence of a thermostable acid alpha-amylase comprising the steps of:
   a) liquefaction of a starch containing material in the presence of an alpha-amylase;
   b) jet cooking the liquefied starch;
   c) followed by a secondary liquefaction in the presence of a thermostable acid alpha-amylase; whereby the enzyme will maintain more than 90% of its activity for 1 hour at 70.degree. C. for thermostability using a DE 12 alpha-amylase TTC liquefied corn starch at 30% dry substance as substrate, pH 5.5, 0.1 M citrate buffer and 4.3 mM $Ca^{+2}$ and the enzyme will maintain more than 70% of its activity in the range from pH 3.8–4.7 using the substrate DE 12 alpha-amylase TTC liquefied corn starch at 30% dry substance, Temperature 40.degree. C., and 0.1 M citrate buffer and 4.3 mM $Ca^{+2}$
   d) saccharification; and
   e) fermentation to produce ethanol;
wherein the steps (a), (b), (c) and (d) is performed in the order (a), (b), (c), (d) and wherein (e) is performed simultaneously to or following (d).

2. The method of claim 1, further comprising recovering the ethanol.

3. The method of claim 1, further comprising a pre-saccharification step which is performed after the secondary liquefaction step (C) and before step (d), wherein the pre-saccharification comprises treating the starch with a glucoamylase at a temperature from 30–65° C.

4. The method of claim 1, wherein the starch containing material is selected from the group consisting of: tubers, roots and whole grain; and any combinations of these.

5. The method of claim 1, wherein the starch containing material is obtained from cereals.

6. The method of claim 1, wherein the starch containing material Is selected from the groups consisting of corns, cobs, wheat, barley, rye, milo and potatoes and any combination of these.

7. The method of claim 1, wherein the starch containing material is whole grain selected from the group consisting of corn, wheat or barley and any combinations of these.

8. The method of claim 1, wherein the starch containing material is whole grain and said method comprises a step of milling the whole grain before step (a).

9. The method of claim 1, wherein the starch containing material is obtainable by a process comprising milling of whole grain.

10. The method of claim 1, further comprising prior to step (a) the steps of;
    i) milling of whole grain;
    ii) forming a slurry comprising the milled grain and water to obtain the starch containing material.

11. The method of claim 9, wherein the milling is a dry milling step.

12. The method of claim 9, wherein the milling is a wet milling step.

13. The method of claim 1, wherein the starch-containing material is a side stream from starch processing.

14. The method of claim 1, further comprising a step of;

(f) distillation to obtain the ethanol;

wherein the fermentation In step (e) and the distillation in step (f) is carried out simultaneously or separately/sequential.

15. The method of claim 14; wherein the starch containing material is milled whole grain, said method further comprising the steps of;

(g) separation of whole stillage produced by of the distillation in step (f), into wet grain and thin stillage; and (h) recycling the thin stillage to the starch containing material prior to step (a).

16. The method of claim 1, wherein the fermentation in step (e) is performed using a yeast.

17. The method of any of claim 1, wherein the fermentation is carried out in the presence of glucoamylase, phytase and/or protease.

18. The method of claim 17, wherein the protease is an acid protease, a neutral protease or an alkaline protease.

19. A method for producing ethanol by fermentation comprising the steps of:

a) liquefaction of a starch containing material in the presence of an alpha-amylase;

b) jet cooking the liquefied starch;

c) followed by a secondary liquefaction in the presence of a thermostable maltogenic acid alpha-amylase; whereby the enzyme will maintain more than 90% of its activity for 1 hour at 70.degree. C. for thermostability using a DE 12 alpha-amylase TTC liquefied corn starch at 30% dry substance as substrate, pH 5.5, 0.1 M citrate buffer and 4.3 mM $Ca^{+2}$ and the enzyme will maintain more than 70% of its activity in the range from pH 3.8–4.7 using the substrate DE 12 alpha-amylase TTC liquefied corn starch at 30% dry substance, Temperature 40.degree. C., and 0.1 M citrate buffer and 4.3 mM $Ca^{+2}$ d) saccharification; and e) fermentation to produce ethanol;

wherein the steps (a), (b), (c) and (d) is performed in the order (a), (b), (c), (d) and wherein (e) is performed simultaneously to or following (d).

\* \* \* \* \*